(12) United States Patent
Huang et al.

(10) Patent No.: US 9,814,663 B2
(45) Date of Patent: *Nov. 14, 2017

(54) PEPTIDE, METHOD AND COMPOSITION FOR INHIBITING MELANOGENESIS

(71) Applicant: RENORIGIN INNOVATION INSTITUTE CO., LTD., Taipei (TW)

(72) Inventors: Hsiu-Chin Huang, Taipei (TW); Hsuan Lin, Taipei (TW)

(73) Assignee: RENORIGIN INNOVATION INSTITUTE CO., LTD., Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/480,515

(22) Filed: Apr. 6, 2017

(65) Prior Publication Data

US 2017/0239163 A1    Aug. 24, 2017

Related U.S. Application Data

(62) Division of application No. 15/051,305, filed on Feb. 23, 2016, now Pat. No. 9,655,834.

(51) Int. Cl.
*A61K 8/64* (2006.01)
*A61Q 19/02* (2006.01)
*A61K 9/00* (2006.01)

(52) U.S. Cl.
CPC .............. *A61K 8/64* (2013.01); *A61K 9/0014* (2013.01); *A61Q 19/02* (2013.01)

(58) Field of Classification Search
None
See application file for complete search history.

(56) References Cited

FOREIGN PATENT DOCUMENTS

WO    WO 2011/126163 A1    10/2011

OTHER PUBLICATIONS

Zimmerman, et al, "Local interation in bends of proteins," PNAS, Oct. 1977, vol. 74, No. 10, pp. 4126-4129.

*Primary Examiner* — James H Alstrum-Acevedo
*Assistant Examiner* — Tara L Martinez
(74) *Attorney, Agent, or Firm* — Birch, Stewart, Kolasch & Birch, LLP

(57) ABSTRACT

An isolated peptide for inhibiting melanogenesis in a mammal subject is provided. The isolated peptide consisting of an amino acid sequence of SSASTTED (SEQ ID NO: 1). Also provided are methods and compositions for inhibiting melanogenesis in a mammal subject.

4 Claims, 3 Drawing Sheets

SEQUENCE LISTING

```
<160> NUMBER OF SEQ ID NOS: 1

<210> SEQ ID NO 1
<211> LENGTH: 8
<212> TYPE: PRT
<213> ORGANISM: Homo sapiens

<400> SEQUENCE: 1

Ser Ser Ala Ser Thr Thr Glu Asp
1               5
```

PEPTIDE, METHOD AND COMPOSITION FOR INHIBITING MELANOGENESIS

This application is a Divisional of U.S. patent application Ser. No. 15/051,305 filed on Feb. 23, 2016, the entire contents of which are hereby incorporated by reference.

FIELD OF THE INVENTION

The present invention relates generally to a peptide for inhibiting melanogenesis or decreasing the melanin content in mammals, and methods and compositions thereof.

BACKGROUND OF THE INVENTION

Human pigmentation results from the synthesis and distribution of melanin most notably in the skin and the hair. Therefore, the color of the skin and the hair depends principally on the types of melanin pigments present and their concentrations.

U.S. Pat. No. 6,579,848 is directed to an agouti signaling protein and peptides as well as pharmaceutical compositions thereof and their use in methods of inhibiting melanin production by melanocytes. U.S. Pat. No. 8,669,238 discloses a method for treating hyperpigmentation comprising administering to a subject having hyperpigmentation, a composition comprising at least one inhibitor selected from the group consisting of a kinesin Kif13A inhibitor, an inhibitor of a sub-unit of AP-1 adaptor complex, and an inhibitor of the interaction between a sub-unit of AP-1 adaptor complex or the AP-1 adaptor complex and kinesin Kif13A. U.S. Pat. No. 8,455,023 relates to a *Cinnamomum subavenium* extract and its use in whitening cosmetology by inhibiting melanogenesis.

BRIEF SUMMARY OF THE INVENTION

It is unexpectedly found in the present invention that a peptide with the sequence SSASTTED (SEQ ID NO: 1) is active in inhibiting or decreasing melanogenesis in a mammal subject.

Accordingly, the present invention provides in one aspect an isolated peptide for inhibiting melanogenesis in a mammal subject or decreasing the melanin content of mammalian melanocytes. The isolated peptide consists of an amino acid sequence of SEQ ID NO: 1.

In another aspect, the present invention features a method for inhibiting melanogenesis in a mammal subject or decreasing the melanin content of mammalian melanocytes, which comprises administering to said subject or said melanocytes an effective amount of an isolated peptide according to the present invention. In preferred embodiments of the invention, the isolated peptide is administered topically to the subject.

In one further aspect, the present invention provides a composition for inhibiting melanogenesis in a mammal subject or decreasing the melanin content of mammalian melanocytes. The composition of the present invention may have a cosmetic use of whitening the skin of human. The composition comprises an effective amount of an isolated peptide consisting of the amino acid sequence of SEQ ID NO: 1. According to certain embodiments of the invention, the composition may further comprise an acceptable carrier, and may be formulated as a topical formulation.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1:
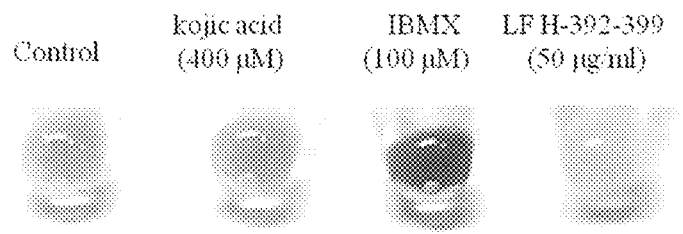
FIG. 1 shows the reduced melanogenesis by the peptide of the invention in cells. B16F10 melanoma cells were treated with 10-50 µg/ml peptide of SEQ ID NO: 1 ("Lf H-392-399") for 5 days with a medium change at day 3. The cells and medium were recovered in test tubes. Kojic acid is used as negative control in the cellular study due to known inhibitory effects on tyrosinase activity. IBMX is used as positive control in the cellular study due to known elevator of cellular cAMP level, to inhibit melanogenesis.

In one aspect, the present invention features an isolated peptide for inhibiting melanogenesis in a mammal subject or decreasing the melanin content of mammalian melanocytes, the isolated peptide consisting of an amino acid sequence of SSASTTED (SEQ ID NO: 1).

In another aspect, the invention provides a method for inhibiting melanogenesis in a mammal subject or decreasing the melanin content of mammalian melanocytes. The method comprises a step of administering to said mammal subject or said mammalian melanocytes the isolated peptide of SEQ ID NO: 1, in an amount effective to inhibit melanogenesis in the mammal subject, or in an amount effective to decrease the melanin content of said melanocytes. Preferably, the isolated peptide is administered topically.

In yet another aspect, the present invention provides a composition comprising an effective amount of an isolated peptide consisting of the amino acid sequence of SEQ ID NO: 1. The composition of the present invention is useful in inhibiting melanogenesis or decreasing the melanin content of melanocytes in mammals. The composition may be used for cosmetic purposes, for example, whitening skin.

In certain embodiments of the invention, the composition further comprises a (physiologically) acceptable carrier.

In some preferred embodiments, the composition of the present invention is formulated as a topical formulation.

Unless defined otherwise, all technical and scientific terms used herein have the same meaning as commonly understood by those of ordinary skill in the art to which this invention belongs.

The use of the word "a" or "an" when used in conjunction with the term "comprising" in the claims and/or the specification may mean "one," but it is also consistent with the meaning of "one or more," "at least one," and "one or more than one."

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

As used herein, the term "carrier" refers to materials commonly used on the formulation of pharmaceutical or cosmetic composition used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" is used herein its conventional sense as referring to a spot which can be in or on any part of the body, including but not limited to the epidermis, any other dermis, or any other body tissue. Topical administration or application means the direct contact of the peptide with tissue, such as skin or membrane which contains melanin-producing cells.

The present invention contemplates the use of the isolated peptide of SEQ ID NO: 1 as an active ingredient for various uses. In one preferred embodiment, the isolated peptide of the present invention is combined with an acceptable carrier to form a topical formulation which may be placed on the skin. Topical formulations may include ointments, lotions, pastes, creams, gels, drops, suppositories, sprays, liquids, powders and transdermal patches. Thickeners, diluents, emulsifiers, dispersing aids or binders may be used as needed. Preferably, one function of the carrier is to enhance skin penetration of the peptide of the present invention, and should be capable of delivering the peptide to melanocytes under in vivo conditions. Suitable carriers are well known to one of ordinary skill, and include but are not limited to water, dimethylsulfoxide, ethanol, liposomes, liquid petrolatum, petrolatum dimethylformamide, 2-pyrrolidone, oleic acid, and Azone® brand penetration enhancer.

The present invention is further illustrated by the following examples, which are provided for the purpose of demonstration rather than limitation.

EXAMPLES

Figure 2A:
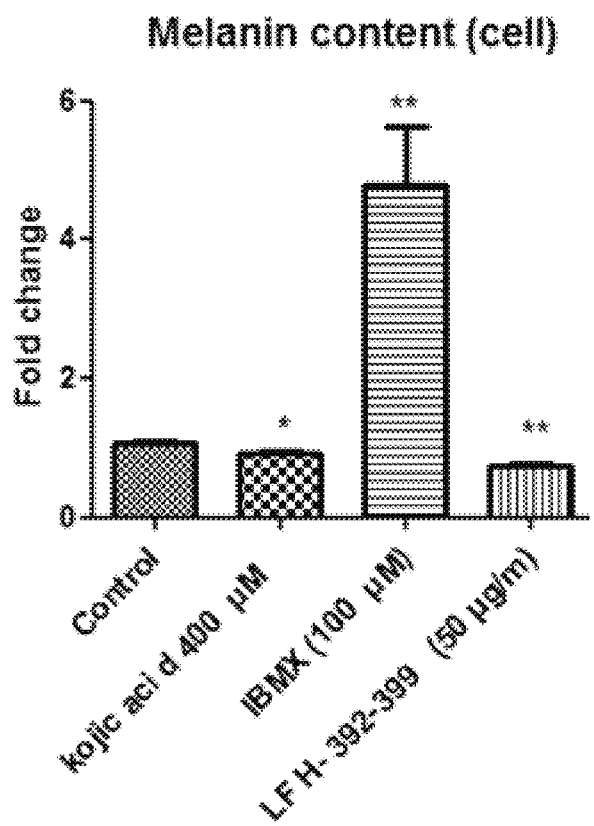
FIG. 2A shows the melanin content in cells.
Figure 2B:
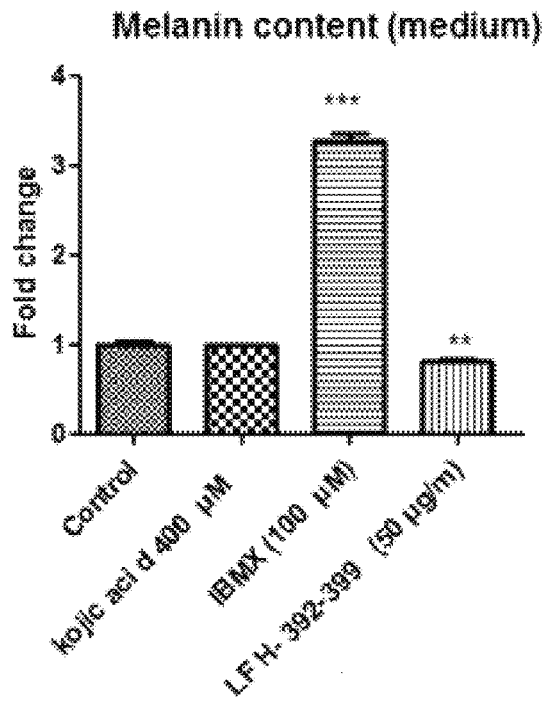
FIG. 2B shows the melanin secretion in culture medium. Each measurement was made in triplicate and data shown represent the mean±S.D. *$p<0.05$ compared to control.
Figure 3:
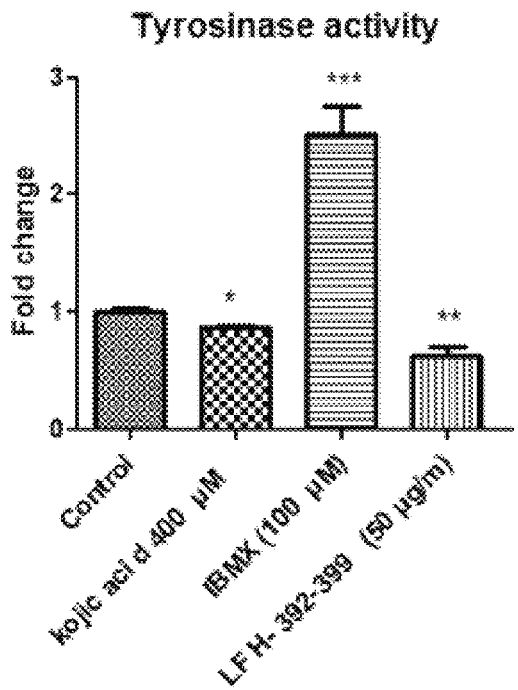
FIG. 3 shows the tyrosinase activity decreased by the peptide of the invention. *$p<0.05$ compared to control.
Figure 4:
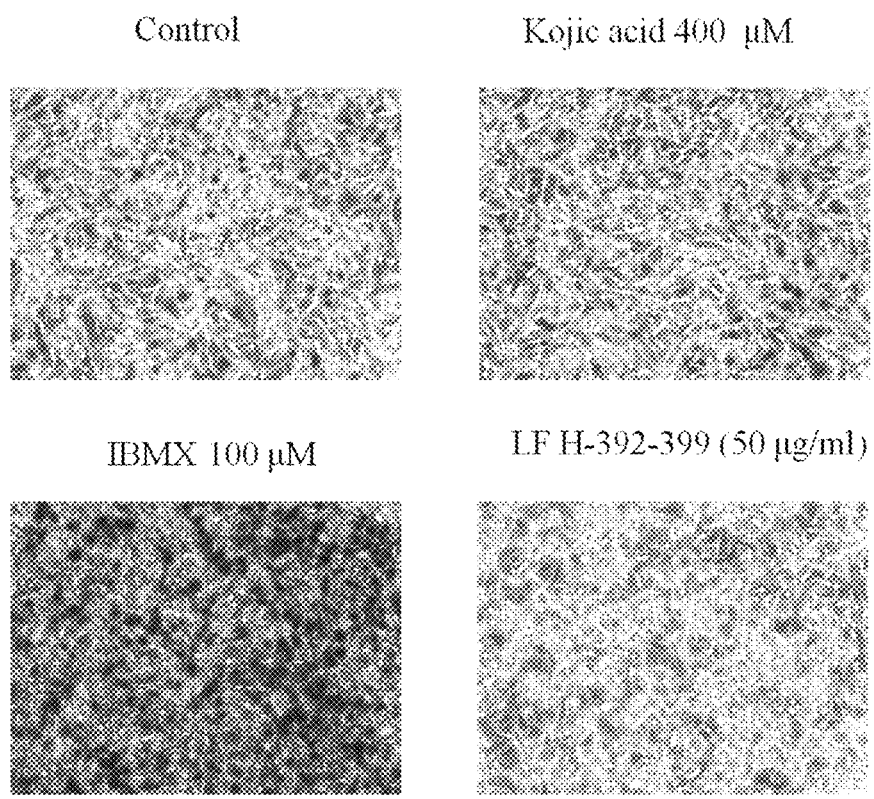
FIG. 4 shows the results of DOPA staining.

Example 1: Peptide of SEQ ID NO: 1 Inhibits Melanogenesis in Mouse Melanoma Cells 1. Materials and Methods
1.1 Preparation of Isolated Peptide of SEQ ID NO: 1
The peptide with the amino acid sequence of SSASTTED (SEQ ID NO: 1) (796.75 Da), derived from human lactoferrin, were synthesized by MDBio, Inc. (Taipei, Taiwan). The purity and composition of the peptide were confirmed by high performance liquid chromatography (HPLC) and mass spectrometry. A 10 mg/ml sample of peptide of SEQ ID NO: 1 was produced by dissolving 10 mg of peptide powder and mixed with 1 ml double deionized water ($ddH_2O$), stored at −20° C. before use.
1.2 Cell Cultures
B16F10 murine melanoma cells were cultured in phenol red-free DMEM with 10% fetal bovine serum and penicillin/streptomycin (100 IU/50 g per mL) in a humidified atmosphere containing 5% $CO_2$ in air at 37° C.
1.3 Melanin Content Assay
Melanin contents of cultured B16F10 cells were measured according to the method (Lee et al., J Invest Dermatol 124, 405-411, 2005) with a slight modification. Briefly, B16F10 cells were seeded in 6-well plate ($2 \times 10^4$ cells/well) and incubated overnight to allow cells to adhere. After treating with various test samples in an incubator for 5 days, washed, trypsinized and counted before pelleting. Melanin per cell was quantified after boiling in 1 M NaOH for 1 hour and melanin content in each sample was read from a calibration curve against synthetic eumelanin at 400 nm and converted to means±SE melanin pg/cell from 3 independent experiments.
1.4 Tyrosinase Assay
Tyrosinase is the rate limiting enzyme in the melanogenic pathway. Its measurement provides a highly specific and sensitive indication of degree of induction of melanogenesis. Tyrosinase enzyme activity of cultured B16F10 cells were measured according to the method of (Bellei et al., J Biol Chem 285, 7288-7299, 2010) with a slight modification. Briefly, B16F10 cells were seeded in 6-well plate ($2 \times 10^4$ cells/well) and incubated overnight to allow cells to adhere. After treating with various test samples in an incubator for 5 days, cells were washed with PBS and then harvested using trypsin. At the end point, the cells were solubilized with phosphate buffer (pH 6.8) containing 1% Triton X-100. The cells were then disrupted by freezing and thawing, and the lysates were clarified by centrifugation at 10,000×g for 10 min. After protein quantification and adjustment of protein concentrations with lysis buffer, 100 µl of each lysate (each containing the same amount of protein) were aliquoted into the wells of a 96-well plate, and 100 µl of 5 mM L-DOPA were then added to each well. The absorbance was measured spectrophotometrically at 475 nm following a 30-min incubation period at 37° C. The measurement was repeated three times.
1.5 DOPA Staining
DOPA staining was also performed to measure tyrosinase enzyme activity. B16F10 cells were seeded in 6-well plate ($2 \times 10^4$ cells/well) and incubated overnight to allow cells to adhere. After treating with various test samples in an incubator for 4 days, cells were washed with PBS, fixation with 2% paraformaldehyde and washing with PBS a further three times, the cells were incubated with 0.1% DOPA (dissolved in 0.1 M PBS) at 37° C. for 5 hour, and observed using light microscopy (Wang et al., Exp Ther Med 6, 967-972, 2013).
2. Results
2.1 Effects on Melanogenesis
Cultures of B16F10 cells treated with 50 µg/ml peptide of SEQ ID NO: 1 ("Lf H-392-399") showed reduced cell pigmentation (FIG. 1).
2.2 Effects on Melanin Contents
B16F10 cells treated with 10 and 50 µg/ml peptide of SEQ ID NO: 1 ("Lf H-392-399") showed significantly decreased melanin synthesis (FIGS. 2A and 2B).
2.3 Effects on Tyrosinase Activity
B16F10 cells treated with 10 and 50 µg/ml peptide of SEQ ID NO: 1 ("Lf H-392-399") showed significantly decreased tyrosinase activity (FIG. 3) and the cells also showed weaker DOPA staining (FIG. 4).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A composition for inhibiting melanogenesis in a mammalian subject, comprising an effective amount of a peptide consisting of the amino acid sequence of SEQ ID NO: 1, the composition being formulated as a topical formulation selected from the group consisting of ointment, lotion, cream and gel.

2. The composition of claim 1, wherein the topical formulation is a lotion or cream.

3. The composition of claim 1, wherein the topical formulation is a gel.

4. The composition of claim 1, wherein the topical formulation is administered via a spray device.

\* \* \* \* \*